United States Patent
Brown

(10) Patent No.: US 8,650,046 B2
(45) Date of Patent: *Feb. 11, 2014

(54) TREATMENT REGIMEN COMPLIANCE AND EFFICACY WITH FEEDBACK

(75) Inventor: Stephen J. Brown, Woodside, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,309

(22) Filed: Sep. 12, 2012

(65) Prior Publication Data

US 2013/0096949 A1    Apr. 18, 2013

Related U.S. Application Data

(63) Continuation of application No. 13/226,063, filed on Sep. 6, 2011, now Pat. No. 8,290,788, which is a continuation of application No. 11/845,317, filed on Aug. 27, 2007, now Pat. No. 8,015,033, which is a continuation of application No. 10/233,296, filed on Aug. 30, 2002, now Pat. No. 7,970,620, which is a continuation-in-part of application No. 09/304,447, filed on May 3, 1999, now abandoned.

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC ........................................................ 705/2–3
See application file for complete search history.

(56) References Cited

U.S. PATENT DOCUMENTS

| | | | | |
|---|---|---|---|---|
| 4,731,726 A | * | 3/1988 | Allen, III | 600/300 |
| 4,950,246 A | * | 8/1990 | Muller | 604/154 |
| 5,019,974 A | * | 5/1991 | Beckers | 600/316 |
| 5,572,421 A | * | 11/1996 | Altman et al. | 705/3 |
| 5,836,304 A | * | 11/1998 | Kellinger et al. | 600/300 |
| 5,950,632 A | * | 9/1999 | Reber et al. | 128/898 |
| 6,151,581 A | * | 11/2000 | Kraftson et al. | 705/3 |

* cited by examiner

*Primary Examiner* — Sheetal R Rangrej
(74) *Attorney, Agent, or Firm* — Maginot, Moore & Beck

(57) ABSTRACT

A method and system for interaction with a community of individuals, relating to compliance with and effectiveness of treatment regimens, including supply and use of pharmaceuticals, using a protocol or other intelligent message which acts in place of a service provider and which is capable of collecting or imparting information to patients in place thereof. Individuals interact with the protocol or intelligent message to provide assistance in all aspects of treatment regimen compliance, data collection, supply or delivery, review and modification.

20 Claims, 5 Drawing Sheets

TREATMENT REGIMEN COMPLIANCE AND EFFICACY WITH FEEDBACK

RELATED APPLICATIONS

This application is a continuation of application Ser. No. 13/226,063, filed Sep. 6, 2011, now U.S. Pat. No. 8,290,788 which is a continuation of application Ser. No. 11/845,317, filed Aug. 27, 2007, now U.S. Pat. No. 8,015,033, which is a continuation of application Ser. No. 10/233,296, filed Aug. 30, 2002, now U.S. Pat. No. 7,970,620, which is a continuation in-part of application Ser. No. 09/304,447, filed May 3, 1999, now abandoned. All of the above-identified applications are incorporated herein by reference in their entirety.

BACKGROUND OF THE INVENTION

1. Field of the Invention

This invention relates to interaction with a community of individuals, relating to treatment regimen compliance and efficacy, including supply and use of pharmaceuticals.

2. Related Art

When medical personnel prescribe treatment regimens for patients or "patients" undertake non-prescription treatment regimens (whether such regimens are prescribed or undertaken for medication, physical therapy, psychological therapy, self-improvement, or other purposes), a problem can arise in assuring that the patients comply with the requirements of the treatment regimen. For example, some patients are disorganized, forgetful, or simply unwilling to comply. When the treatment regimen has potential side effects, or when the treatment regimen is to be followed under stated conditions (for example: taking medicine with meals, not with alcohol, or in the evening), patient compliance can be relatively reduced even further. When the treatment regimen is relatively complex, some patients are even unable or unwilling to manage that treatment regimen.

Known methods for monitoring and controlling treatment regimens are relatively costly and limited in capability. Some known methods are described in the following patents:

U.S. Pat. No. 5,408,443, "Programmable Medication Dispensing System," issued Apr. 18, 1995 in the name of Edward D. Weinberger.

U.S. Pat. No. 5,642,731, "Method of and Apparatus for Monitoring the Management of Disease," issued Jul. 1, 1997 in the name of Bruce A. Kehr.

U.S. Pat. No. 5,752,235, "Electronic Medication Monitoring and Dispensing Method," issued May 12, 1998 in the name of Bruce A. Kehr, et al.

While these known methods generally achieve the goal of monitoring and controlling a treatment regimen, particularly a medication regimen, they suffer from several drawbacks and limitations.

First, there is a need to provide a portable system to monitor and encourage compliance, and facilitate data collection, so that patients are restricted as little as possible regarding their activities and movements.

Second, there is a need to determine if patients are actually complying with treatment regimens at times when the patients are relatively remote to client devices for the system. Known methods do not provide adequate feedback to determine whether patients are complying with the treatment regimen unless they remain relatively local to client devices.

Third, there is a need to determine whether treatment regimens have the desired and intended effects. Known methods do not provide adequate feedback to determine whether treatment regimens are effective, or whether patients are suffering any untoward side effects. Using known methods, medical personnel must generally wait for patients to complain, or for medical tests to show, that prescribed treatment regimens are inadequate or are producing side effects. Similarly, using known methods, patients undertaking non-prescribed treatment regimens generally do not have effective or convenient systems to monitor and record whether non-prescribed treatment regimens are producing intended results.

Fourth, there is a need to inform patients to follow treatment regimens, particularly when patients are forgetful or treatment regimens are complex. Although known methods do include reminders to patients, it would be advantageous to tailor those reminders to patients' actual compliance history (thus, providing fewer reminders when they are relatively less necessary and more reminders when they are relatively more necessary).

Fifth, there is a need to leverage expert knowledge to improve response to feedback from patients, and to reduce the time and expense required for medical personnel to individually monitor, evaluate and modify treatment regimens.

Sixth, there is a need to broaden application of reminder and expert knowledge leveraging systems beyond medication regimens, to include physical, psychological, self-improvement and other treatment regimens.

Accordingly, it would be advantageous to provide a portable device that can be coupled and uncoupled to a communication system with feedback to monitor patient compliance with, and effectiveness of, treatment regimens, so that input from patients regarding treatment regimens can be recorded, reviewed, analyzed and otherwise generally acted upon. Medical personnel and/or patients can thus (1) monitor compliance with treatment regimens, (2) monitor effectiveness or side effects of treatment regimens, (3) remind patients no more than necessary, and (4) possibly alter treatment regimens in response to feedback from patients. These advantages are achieved in embodiments of the invention in which a portable device is intermittently coupled to a client device in a client-server system, the patient enters information to the portable device about following the treatment regimen while the portable device is uncoupled, and medical personnel or the patient can receive that information and possibly alter the behavior of the portable device when the portable device is re-coupled to the system.

SUMMARY OF THE INVENTION

The invention provides a method and system for interaction with a community of individuals, relating to compliance with and effectiveness of treatment regimens, including supply and use of pharmaceuticals, using a protocol or other intelligent message which acts in place of a service provider and which is capable of collecting or imparting information to patients in place thereof. Individuals interact with the protocol or intelligent message to provide assistance in all aspects of treatment regimen compliance, data collection, supply or delivery, review and modification. These aspects can include (1) reminders regarding compliance with a selected treatment regimen for medication, physical therapy, psychological therapy, self-improvement, or some combination thereof, (2) data collection of facts regarding patient compliance, symptomology, possible drug interactions or side effects of medication if required by the treatment regimen, and other facts relevant to evaluation and possible modification of the treatment regimen; (3) networked integration with workstations for medical professionals to automate approvals and modifications, and refills and delivery of medication if required by the treatment regimen.

A system includes a set of client devices and a server device. A service provider determines a treatment regimen for selected patients, determines a protocol to be followed by the client devices to assist the patient in complying with that treatment regimen [in assisting with that medication regimen] and to maximize effectiveness of treatment, and sends that protocol to the server device. The server device can update (responsive to the protocol) selected instructions at the client devices, and can receive (responsive to selected instructions) information from the client devices regarding their associated patients.

In a first preferred embodiment, a client device, located locally to a patient, couples to a portable device (such as a cellular telephone, pager, "Palm Pilot" or other handheld computer, or watch), capable of being carried away by the patient to locations relatively remote from the client device. The client device can interact with the portable device: (1) to provide the portable device with the capability of reminding the patient regarding the treatment regimen, or (2) to provide the portable device with the capability of further data collection regarding the patient. The client device can interact with the portable device using a docking connection, an infrared connection, a radio-frequency connection, a plug-in connection, or another suitable connection.

DETAILED DESCRIPTION OF THE PREFERRED EMBODIMENT

In the following description, a preferred embodiment of the invention is described with regard to preferred process steps and data structures. Embodiments of the invention can be implemented using general purpose processors or special purpose processors operating under program control, or other circuits, adapted to particular process steps and data structures described herein. Implementation of the process steps and data structures described herein would not require undue experimentation or further invention.

System Elements

Figure 1:
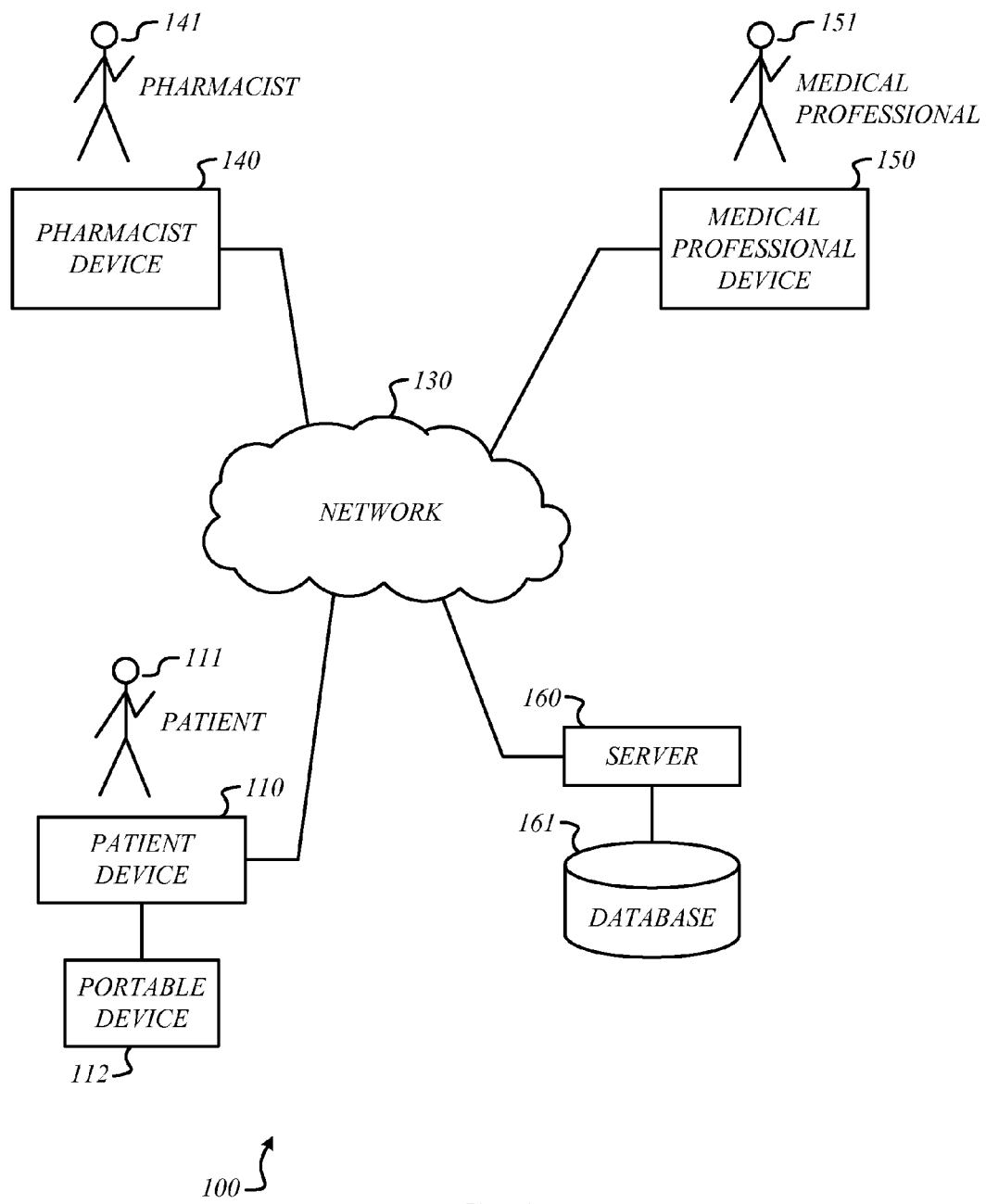
FIG. 1 shows a block diagram of a system to encourage and monitor compliance with a treatment regimen using a protocol or other intelligent message which acts in place of a service provider to collect and impart information relevant to the treatment regimen.

FIG. 1 shows a block diagram of a system 100 to encourage and monitor compliance with a treatment regimen using a protocol or other intelligent message which acts in place of a service provider to collect and impart information relevant to the treatment regimen, including a patient device 110, a pharmacist device 140, a medical professional device 150, and a server device 160, said devices being coupled using a communication network 130, and a portable device 112 which can be coupled to the patient device 110 to receive information regarding the treatment regimen and send feedback from the patient 111 responsive thereto.

For further information regarding a data structure and simplified patient interaction interface, and preferred embodiments of the patient device 110, pharmacist device 140, medical professional device 150, and the server device 160 including database 161 of treatment regimen information, see related application Ser. No. 09/201,323, Express Mail Mailing No. EE143637591US, filed Nov. 30, 1998, in the name of Stephen J. Brown, titled "Leveraging Interaction with A Community of Individuals," assigned to the same assignee, and other related applications incorporated by reference therein.

For further information regarding the protocol or other intelligent message used by the system, see related application Ser. No. 09/203,882, Express Mail Mailing No. EE143637565US, filed Dec. 1, 1998, in the name of Stephen J. Brown, titled "Remote User Data Collection Protocols Including Data Structures and User Interface," assigned to the same assignee, and other related applications incorporated by reference therein.

For further information regarding a medicine dispenser which can be used by the system, see related application Ser. No. 09/203,880, Express Mail Mailing No. EE143637557US, filed Dec. 1, 1998, in the name of Stephen J. Brown, et al., titled "Using A Computer Communication System With Feedback to Dispense Medicine," assigned to the same assignee, and other related applications incorporated by reference therein.

Portable Device

Figure 3:
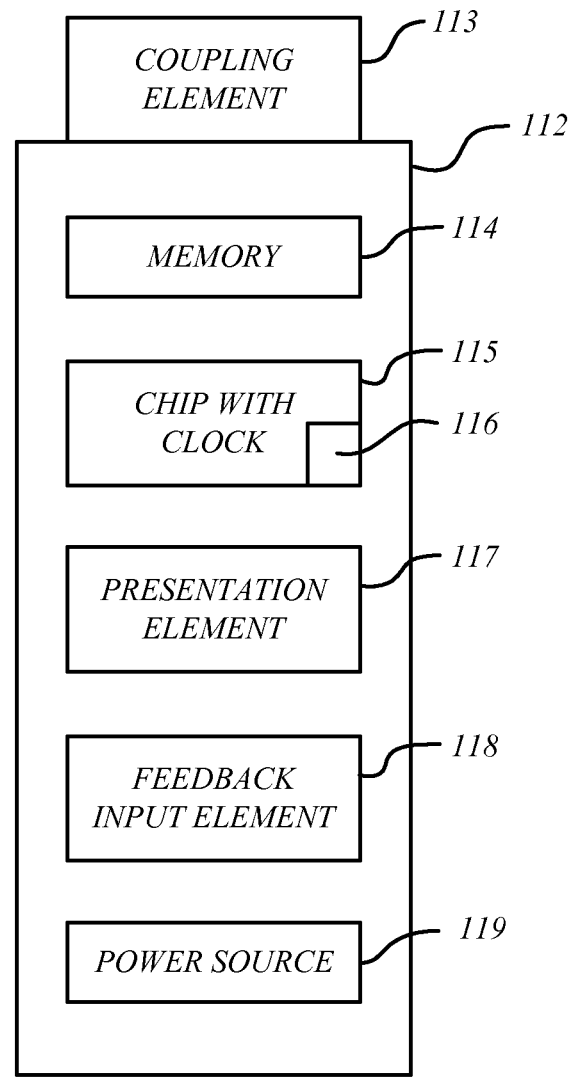
FIG. 3 shows a first preferred embodiment of a portable device used by the system to encourage and monitor compliance with a treatment regimen, and to collect and impart information relevant to the treatment regimen.

FIG. 3 shows a first preferred embodiment of a portable device 112 used by the system 100.

In a first preferred embodiment, the portable device 112 includes a coupling element 113 for coupling the portable device 112 to the patient device 110, a memory element 114, a processor chip 115 including a clock circuit 116, a presentation element 117, and a patient feedback input element 118.

A service provider determines a treatment regimen for selected patients 111 and a protocol to be followed by their portable devices 112 to assist the patients 111 in following the treatment regimen. The service provider sends the treatment regimen and protocol to the server device 160 where it is recorded in the database 161. The server device 160 sends the treatment regimen and protocol information to the patient device 110, and optionally to the pharmacist device 140 and the medical professional device 150.

The portable device 112 is coupled to the patient device 110 using the coupling element 113. The coupling element 113 may couple using a docking station, an infrared connection, a radio-frequency connection, a plug-in connection, other suitable means or any variant thereof.

While coupled, the treatment regimen and protocol information received by the patient device 110 is sent to the portable device 112 and recorded in the memory 114. In a first preferred embodiment, the power source 119 is rechargeable and the charge can be replenished by the patient device 110 while the portable device 112 is coupled to it. In alternative embodiments, the power source 119 is rechargeable and the charge can be replenished by some other device, or includes one or more disposable batteries.

After the treatment regimen and protocol information is recorded in the memory 114, the portable device 112 can be uncoupled from the patient device 110 and taken with the patient 110 to locations relatively or logically remote from the patient device 110. Whether the portable device 112 coupled or uncoupled to the patient device 110, when the patient 111 is due to perform an act according to the treatment regimen, the portable device 112 uses the presentation element 117 to provide a reminder message instructing the patient 111 to perform that act. In a first preferred embodiment, the act to be performed is related to compliance with a medication regimen including, without limitation, obtaining medicine, taking medicine, taking medicine with another substance such as food or water, not taking medicine with another substance such as alcohol or incompatible medications, or obtaining a prescription refill. In alternative embodiments, the act to be performed may be pursuant to a physical therapy regimen including, without limitation, exercising, stretching, changing position, or changing work routine; pursuant to a psychological therapy regimen including, without limitation, repeating an affirmation, meditation, self-hypnosis or other mental activity; or pursuant to a self-help regimen or other type of treatment regimen such as weight loss including, without limitation, drinking water or eating a snack.

The patient 111 performs the indicated act and enters a message into the portable device 112 confirming performance of the act using the patient feedback input element 118. Operation of the patient feedback input element 118 causes the processor chip 115 to cancel the reminder message, check the clock 116, and record the time and fact of performance in the memory 114. In a first preferred embodiment, the patient 111 also enters additional information relevant to monitoring and evaluating the treatment regimen in response to queries by the presentation element 117 in accordance with the treatment regimen and protocol.

The number of reminder messages provided to the patient 111, and the number of messages from the patient 111 confirming performance of the indicated acts and/or providing other information relevant to compliance with and effectiveness of the treatment regimen, is limited only by the memory capacity of the portable device 112.

In a first preferred embodiment, the presentation element 117 is a human-readable visual display using LCD's, LED's, or other suitable devices. In alternative preferred embodiments, the presentation element 117 can be a device which produces human-intelligible sound, or a combination of devices which produce human-intelligible visual and audible signals.

At some later time, the portable device 112 is re-coupled to the patient device 110 using the coupling element 113, causing the contents of the memory 114 to be downloaded into the patient device 110 and sent to the server device 160 for recording in the database 161. Such a time may be as is convenient to the patient 111, or according to a selected maximum time interval dictated by the treatment regimen and protocol, or as is required to replenish the power source 119 of the portable device 112, or in accordance with other requirements of the system 100.

At the server device 160, the protocol or other intelligent message reviews and compares the information provided by the patient 111 to the requirements of the treatment regimen in order to evaluate the effectiveness of the treatment regimen towards achieving treatment objectives and as to compliance of the patient 111 with the treatment regimen. The protocol may then leave the treatment regimen unchanged or modify it as needed to increase effectiveness and/or compliance; in either case, the server device 160 sends a message to the patient device 110 as to the regimen to be followed from that time forward. In a preferred embodiment, the server device 160 also sends that message to the pharmacist device 140 and the medical professional device 150. For additional information regarding the protocol used by the system 100 and interaction of the protocol with other elements of the system 100, see discussion above at System Elements regarding related applications.

In a first preferred embodiment, information regarding the entire course of the treatment regimen, such as each updated regimen and its effectiveness and relative compliance by the patient can be stored by each of those devices and displayed on demand. In alternative embodiments, only the server records the entire course, or only selected devices, or some combination thereof.

In a preferred embodiment, when a treatment regimen requires a patient 111 to take one or more medications, the portable device 112 can be coupled to a medication dispenser containing medication specified by the treatment regimen. In an alternative embodiment, the portable device 112 also controls the medication dispenser so as to release only the correct dosage of the correct medication at the correct time responsive to the treatment regimen. In a further alternative preferred embodiment, the dispenser automatically provides feedback to the portable device 112 when the correct medication is removed, canceling the reminder message and storing the feedback for subsequent downloading to the patient device 110 on the next occasion that the portable device 112 is coupled to the patient device 110.

The patient device 110 can be any device for electronic communication including, but not limited to, an application specific device, a hard-wired telephone, a cellular telephone, a pager, a personal desktop computer, a personal notebook computer, a hand-held computing device, an internet appliance, an internet-enabled television such as WebTV, personal digital assistant such as the Palm III, or any variant thereof.

The portable device 112 can be any portable device for electronic communication which is capable of being coupled to the patient device 110 including, without limitation, an application specific device, a cellular telephone, a pager, a personal notebook computer, a hand-held computing device, an internet appliance, a personal digital assistant such as the Palm III, a watch, or any variant thereof.

The feedback input element 118 can be any means of providing input to an electronic communication device including, but not limited to, a button, a telephone key, a computer keyboard key, a voice-response activator, or any variant or combination thereof.

Method of Operation

Figure 2:
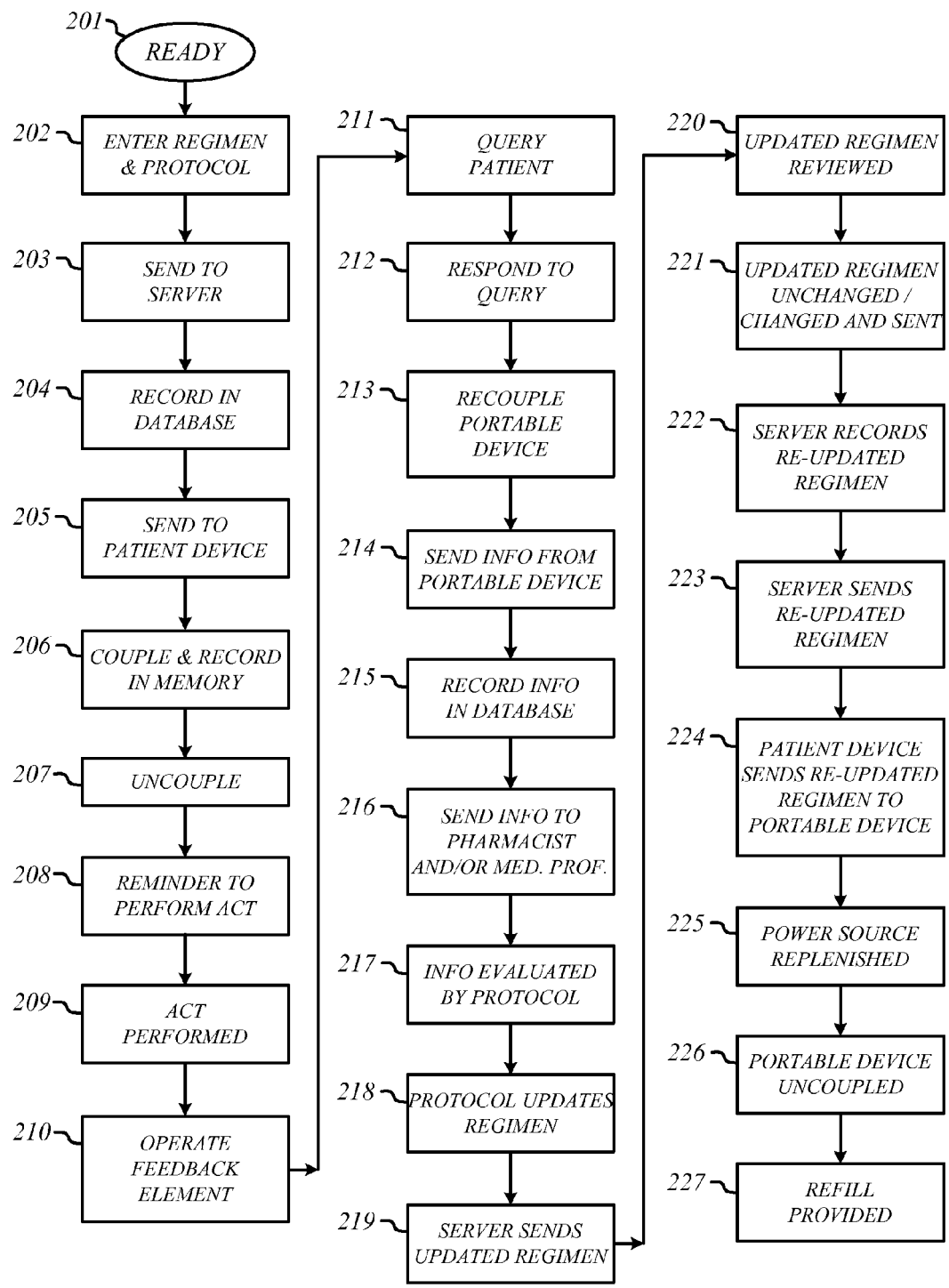
FIG. 2 shows a process flow diagram of a method for operating a system for interaction with a community of individuals to encourage and monitor compliance with a treatment regimen, using a protocol or other intelligent message which acts in place of a service provider to collect and impart information relevant to the treatment regimen.

FIG. 2 shows a process flow diagram of a method for operating a system for leveraging expert interaction with a community of individuals to encourage compliance with a treatment regimen and for collecting and imparting information relevant to that treatment regimen.

A method 200 is performed by the system 100, as follows:

At a flow point 201, the system 100 is ready to proceed.

At a step 202, a service provider enters information concerning a treatment regimen and protocol to be followed by the patient 111.

At a step 203, the treatment regimen and protocol information is sent to the server device 160 using the communications network 130.

At a step 204, the server device 160 records the treatment regimen and protocol information received from the service provider in the database 161.

At a step 205 in a preferred embodiment, the server device 160 sends the treatment regimen and protocol information to the patient device 110, the pharmacist device 140 and the medical professional device 150 using the communication network 130. In alternative embodiments, the server device 160 may send the treatment regimen and protocol information only to the patient device 110.

At a step 206, the portable device 112 is coupled to the patient device 110 and the treatment regimen and protocol information is copied into the memory 114 of the portable device 112.

At a step 207, the portable device 112 is uncoupled from the patient device 110 and is taken with the patient 111 to a location relatively remote from the patient device 110.

At a step 208, responsive to the treatment regimen and protocol information stored in the memory 114 in conjunction with input from the clock 116, the patient device 110 uses the presentation element 117 to provide a reminder message to the patient 111 that an act is required to be performed by the patient 111 and instructs the patient 111 regarding the act to be performed.

At a step 209, the patient 111 performs the indicated act as directed.

At a step 210, the patient 111 operates the feedback input element 118 on the portable device 112, canceling the reminder message.

At a step 211, the portable device 112 uses the presentation element 117 to query the patient 111 to provide information responsive to the protocol for evaluating the effectiveness of the treatment regimen.

At a step 212, the patient 111 operates the feedback input element 117 to provide information responsive to the queries, and that information is recorded in the memory 114.

At a step 213, the portable device 112 is re-coupled to the patient device 110.

At a step 214, the information stored in the memory 114 is sent to the patient device 110, which in turn sends that information to the server device 160 using the communication network 130.

At a step 215, the information received by the server device 160 is recorded in the database 161.

At a step 216, in a preferred embodiment the server device 160 sends the information received from the patient device 110 to the pharmacist device 140 and to the medical professional device 150 using the communication network 130. In an alternative embodiment, the server device 160 does not send the information received from the patient device 110 to the pharmacist device 140 or to the medical professional device 150, whether using the communication network 130 or otherwise.

At a step 217, the information received by the server device 160 from the patient device 110 is evaluated by the protocol.

At a step 218, the protocol updates the treatment regimen and either leaves it unchanged or modifies it in accordance with the protocol logic.

At a step 219 in a preferred embodiment, the server device 160 sends the updated treatment regimen information to the patient device 110, to the pharmacist device 140 and to the medical professional device 150, using the communication network 130. In an alternative embodiment, the server device 160 does not sent the updated treatment regimen information to the pharmacist device 140 or the medical professional device 150.

At a step 220 in a preferred embodiment, the pharmacist 141 and/or the medical professional 151 review and compare the original treatment regimen, the compliance and other information input by the patient 111, and the updated treatment regimen, and either leave the updated treatment regimen and protocol information unchanged or modify it as necessary. In an alternative embodiment, step 220 does not take place.

At a step 221 in a preferred embodiment, the treatment regimen and protocol information as unchanged or as modified by the pharmacist 141 and/or the medical professional 151 is sent to the server device 160 using the communication network 130. In an alternative embodiment, step 221 does not take place.

At a step 222, the server device 160 records the treatment regimen and protocol information as unchanged or as modified by the pharmacist 141 and/or the medical professional 151 in the database 161. In an alternative embodiment, step 222 does not take place.

At a step 223 in a preferred embodiment, the server device 160 sends the treatment regimen and protocol information as unchanged or as modified by the pharmacist 141 and/or the medical professional 151 to the patient device 110 using the communication network 130. In an alternative embodiment, step 223 does not take place.

At a step 224, the patient device 110 sends the updated treatment regimen information to the portable device 112 and it is recorded in the memory 114.

At a step 225, the patient device 110 replenishes the charge of the power source 119.

At a step 226, the patient 111 uncouples the portable device 112 from the patient device 110.

At a step 227, the pharmacist 141 provides a refill or new medicine to the patient 111 responsive to the treatment regimen and protocol information. In an alternative embodiment, step 227 does not take place.

Figure 4:
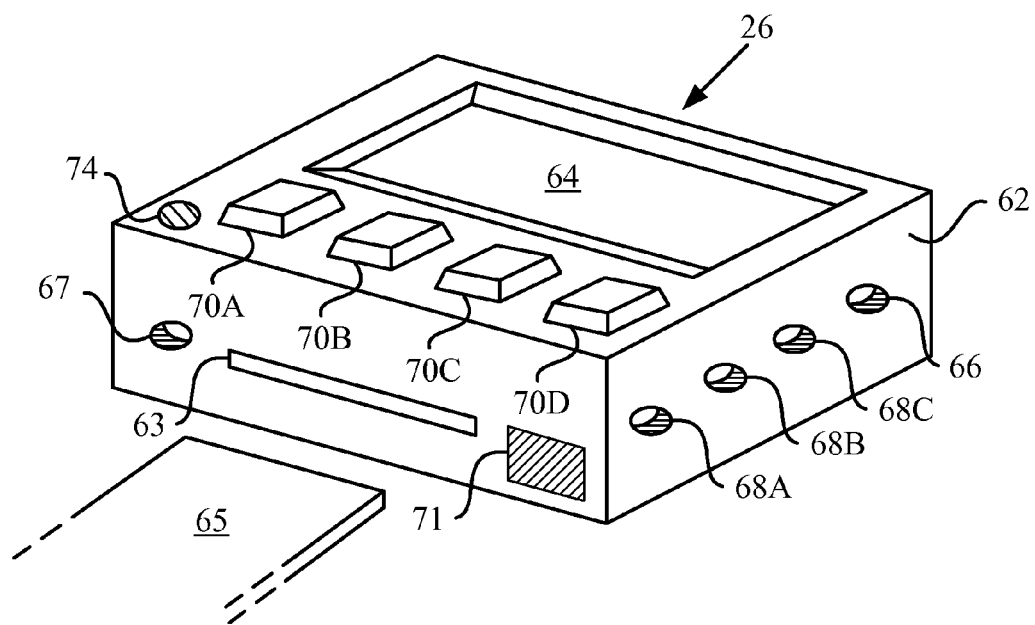
FIG. 4 is a perspective view of a remotely programmable apparatus.
Figure 5:
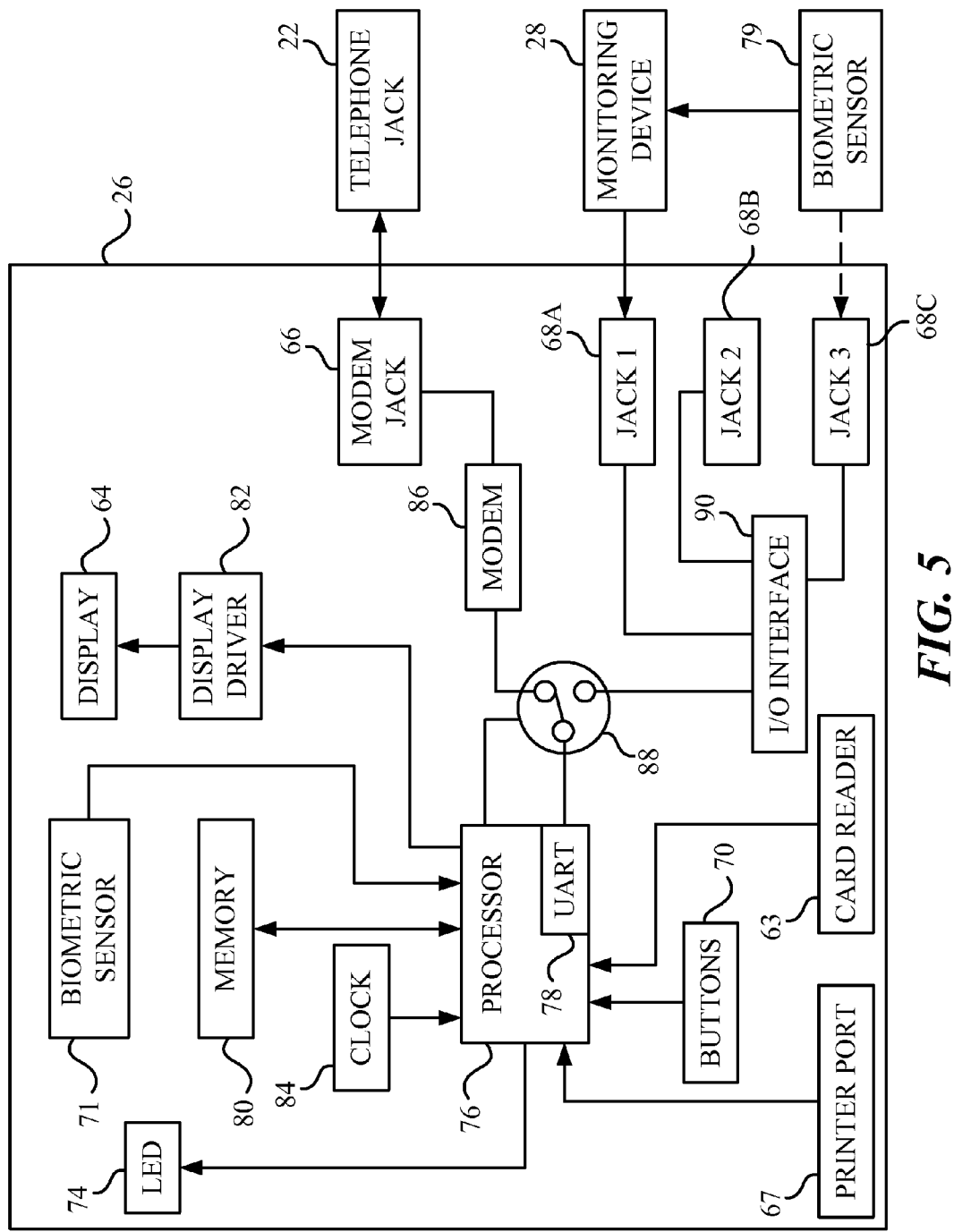
FIG. 5 is a block diagram illustrating the components of the apparatus of FIG. 4.

FIGS. 4-5 show the structure of an apparatus 26 according to the preferred embodiment. The remotely programmable apparatus has a communication device, such as a modem, for receiving the script programs from the server and for transmitting the responses to the server. The remotely programmable apparatus also has a user interface for communicating the query sets to the individuals and for receiving the responses to the query sets. In the preferred embodiment, the user interface includes a display for displaying the query sets and user input buttons for entering the responses to the query sets. In an alternative embodiment, the user interface includes a speech synthesizer for audibly communicating the query sets and a speech recognizer for receiving spoken responses to the query sets.

The remotely programmable apparatus also includes a memory for storing the script programs and the responses to the query sets. The remotely programmable apparatus further includes a microprocessor connected to the communication device, the user interface, and the memory. The microprocessor executes the script programs to identify the individual, communicate the query sets to the individual, receive the responses to the query sets, and transmit the responses to the server through the communication network.

In one embodiment, the system also includes at least one monitoring device for producing measurements of a physiological condition of the individual and for transmitting the measurements to the apparatus. The monitoring device can also be used to help the remotely programmable apparatus identify the individual. The remotely programmable apparatus includes a device interface connected to the microprocessor for receiving the measurements from the monitoring device. The measurements are stored in the memory and transmitted to the server along with the individual's identity and the responses to the query sets. The server also preferably includes a report generator connected to the database for generating a report of the measurements and responses. The report is displayed on the workstation.

As the present invention has multi-user capabilities, it must identify each individual or individual type in order to select the correct script program. In one embodiment, the individual can enter his or her unique identification code into the remotely programmable apparatus. The code is sent to the server and used to determine which script program to send back to the apparatus.

In another embodiment, the system uses a data card, which contains information about an individual's identity. The remotely programmable apparatus includes a data card reader in which the data card can be placed and read. A personal identification number (PIN) can also be used in conjunction with the data card in order confirm an individual's identity. In this embodiment, the present invention resembles an ATM machine.

In yet another embodiment, the system utilizes a biometric information gathered using a biometric sensor to determine an individual's identity. The biometric information is used by the methods and systems of the invention to assign script programs, to customize script programs for the identified individual and to provide security against unauthorized use for either or both the remote apparatus and server systems. Examples of biometric information useable by the invention include: retina metrics, iris metrics, voice print metrics, body measurement metrics, handwriting metrics, body odor metrics, heart beat signature metrics and biometrics that may be discernable from the individual's body fluids such as blood, urine or breath.

Table 1 shows an exemplary listing of script commands used in the preferred embodiment of the invention.

Referring to FIG. 4, apparatus 26 includes a housing 62. Housing 62 is sufficiently compact to enable apparatus 26 to be placed unobtrusively on a pharmacy counter or check stand counter. Apparatus 26 also includes a display 64 for displaying queries and prompts to the patient. In the preferred embodiment, display 64 is a liquid crystal display (LCD).

Four user input buttons 70A, 70B, 70C, and 70D are located adjacent display 64. User input buttons 70A, 70B, 70C, and 70D are for entering in apparatus 26 responses to the queries and prompts. In the preferred embodiment, user input buttons 70A, 70B, 70C, and 70D are momentary contact push buttons. In alternative embodiments, user input buttons 70A, 70B, 70C, and 70D may be replaced by switches, keys, a touch sensitive display screen, or any other data input device.

Three monitoring device jacks 68A, 68B, and 68C are located on a surface of housing 62. Device jacks 68A, 68B, and 68C are for connecting apparatus 26 to a number of monitoring devices 28, such as blood glucose meters, respiratory flow meters, or blood pressure cuffs, through respective connection cables (not shown). Apparatus 26 also includes a modern jack 66 for connecting apparatus 26 to a telephone jack through a standard connection cord (not shown). Apparatus 26 further includes a visual indicator, such as a light emitting diode (LED) 74. LED 74 is for visually notifying the patient that he or she has unanswered queries stored in apparatus 26.

TABLE 1

SCRIPT COMMANDS

| Command | Description |
|---|---|
| CLS: {LF} | Clear the display. |
| ZAP: {LF} | Erase from memory the last set of query responses recorded. |
| LED: b {LF} | Turn the LED on or off, where b is a binary digit of 0 or 1. An argument of 1 turns on the LED, and an argument of 0 turns off the LED. |
| DISPLAY: {chars} {LF} | Display the text following the DISPLAY command. |
| INPUT: mmmm{LF} | Record a button press. The m's represent a button mask pattern for each of the four input buttons. Each m contains an "X" for disallowed buttons or an "O" for allowed buttons. For example, INPUT: OXOX {LF} allows the user to press either button #1 or #3. |
| WAIT: {LF} | Wait for any one button to be pressed, then continue executing the script program. |
| COLLECT: device {LF} | Collect measurements from the monitoring device specified in the COLLECT command. The user is preferably prompted to connect the specified monitoring device to the apparatus and press a button to continue. |
| NUMBER: aaaa {LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t {LF} | Wait until time t specified in the DELAY command, usually the prescribed connection time. |
| CONNECT: {LF} | Perform a connection routine to establish a communication link to the server, transmit the patient or patient type identification code, query responses, device measurements, and script identification code to the server, and receive and store a new script program. When the server instructs the apparatus to disconnect, the script interpreter is restarted, allowing the new script program to execute. |

The script commands illustrated in Table 1 are representative of the preferred embodiment and are not intended to limit the scope of the invention. After consideration of the ensuing description, it will be apparent to one skilled in the art that many other suitable scripting languages and sets of script commands may be used to implement the invention.

Apparatus 26 also contains a data card reader 63. Data card reader 63 is capable of reading a data card 65 containing information about a patient. In the present invention, data card 65 contains the patient's identity, condition or disease, and possibly prescription information. Data card 65 is placed in data card reader 63, thus allowing apparatus 26 to identify the patient and assign script program 40. Apparatus 26 also has a printer port 67, allowing apparatus 26 to be directly connected to a printer. Queries 94, responses 42, device measurements 44, and other pertinent information stored on apparatus 26 can be printed directly.

The apparatus also includes a biometric sensor 71 for gathering biometric information from the user. Examples of biometric sensors that may be used by the apparatus 26 include an optical device (e.g., a camera created from a CCD), a silicon sensor (e.g., a chip that gathers information using the capacitance occurring as a result of a body part coming into contact with the silicon chip), a sound sensor (e.g., a microphone), an olfactory sensor (e.g., an "artificial nose") and/or a sensor for measuring three dimensional biometric topology (e.g., a laser or ultrasound measuring device). The type of biometric sensor 71 used in an embodiment of the invention corresponds to the type of biometric information used by the methods of the invention.

The present invention may use any type of biometric information gathering and analysis as described herein or known to those skilled in the art. Biometric information includes information that when used alone or in combination with other information uniquely identifies an individual with reasonable certainty. Examples of biometric information include: retina metrics, iris metrics, voice print metrics, body measurement metrics, handwriting metric, body odor metrics, heart beat signature metrics and biometrics that may be discernable from the individual's body fluids such as blood, urine or breath. Retina metrics make use of individual blood vessel patterns on the retina of the eye which are photographed, encoded, and compared to a previously coded "enrollment." Iris metrics similarly refer to individualized patterns in the iris of the eye which are photographed, encoded, and compared to a previously coded "enrollment." Voice print metrics capture a sample of an individual voice which reflect the physical structure producing the voice and the developmental speech patterns. Body measurement metrics map the physical measurement of the body and may include the physical characteristics of a finger, a hand, a face or other parts of the body. Handwriting metrics may include not only a comparison of the handwriting to a know sample, but also characteristics such as the speed, stroke order and pressure associated with, for instance, a signature. Use of physiological measurements as biometric information is discussed in more detail below.

FIG. 5 is a schematic block diagram illustrating the components of apparatus 26 in greater detail. Apparatus 26 includes a microprocessor 76, and a memory 80 connected to microprocessor 76. Memory 80 is preferably a non-volatile memory, such as a serial EEPROM. Memory 80 stores script programs 40 received from server 18, measurements 44 received from monitoring device 28, responses to queries, and a patient or patient type's unique identification code. Unique information for identifying the individual may also be stored in the memory 80 of the apparatus 26, by the server 18, or both. This unique information may include a unique identification number or biometrics information about the individual that uniquely identifies that individual. Microprocessor 76 also includes built-in read only memory (ROM) which stores firmware for controlling the operation of apparatus 26. The firmware includes a script interpreter used by microprocessor 76 to execute script programs 40. The script interpreter interprets script commands which are executed by microprocessor 76.

The script commands allow apparatus 26 to identify the patient or patient type through user buttons 70A, 70B, 70C, and 70D, monitoring device 28, data card 65, or printer port 67. They also allow apparatus 26 to display the query sets to the patient, receive responses 42 to the query sets, receive measurements 44 from monitoring device 28, and transmit responses to server 18. Specific techniques for interpreting and executing script commands in this manner are well known in the art.

Microprocessor 76 is preferably connected to memory 80 using a standard two-wire $I^2C$ interface. Microprocessor 76 is also connected to user input buttons 70A, 70B, 70C, and 70D, data card reader 63, printer port 67, LED 74, a clock 84, and a display driver 82. Clock 84 indicates the current date and time to microprocessor 76. For clarity of illustration, clock 84 is shown as a separate component, but is preferably built into microprocessor 76. Display driver 82 operates under the control of microprocessor 76 to display information on display 64. Microprocessor 76 is preferably a PIC 16C65 processor which includes a universal asynchronous receiver transmitter (UART) 78. UART 78 is for communicating with a modem 86 and a device interface 90. A CMOS switch 88 under the control of microprocessor 76 alternately connects modem 86 and interface 90 to UART 78.

Modem 86 is connected to a telephone jack 22 through modem jack 66. Modem 86 is for exchanging data with server 18 through communication network 24. The data includes script programs 40 which are received from server 18 as well as responses 42 to queries, device measurements 44, script identification codes, and the patient or patient type's unique identification code or other information that uniquely identifies the individual which modem 86 transmits to server 18. Modem 86 is preferably a complete 28.8 K modem commercially available from Cermetek, although any suitable modem may be used.

Device interface 90 is connected to device jacks 68A, 68B, and 68C. Device interface 90 is for interfacing with a number of monitoring devices, such as blood glucose meters, respiratory flow meters, blood pressure cuffs, weight scales, or pulse rate monitors, through the device jacks. Device interface 90 operates under the control of microprocessor 76 to collect measurements 44 from the monitoring devices and to output the measurements to microprocessor 76 for storage in memory 80. In the preferred embodiment, device interface 90 is a standard RS232 interface. For simplicity of illustration, only one device interface is shown in FIG. 4. However, in alternative embodiments, apparatus 26 may include multiple device interfaces to accommodate monitoring devices 28 which have different connection standards.

The monitoring device 28 may include a biometric sensor 79 in lieu of or in addition to a biometric sensor 71 made part of the apparatus 26. In addition to the types of biometric sensors 71 discussed above, a biometric sensor 79 may utilize or augment the data gathered by the monitoring device 28. For example, the biometric sensor 79 may make use of a heartbeat signature obtained by a pulse rate monitor, the blood characteristic obtained using a blood glucose meter, or the signature antigens present in a device reading a urine sample.

Alternative Embodiments

Although preferred embodiments are disclosed herein, many variations are possible which remain within the concept, scope, and spirit of the invention, and these variations would become clear to those skilled in the art after perusal of this application.

The invention claimed is:

1. A portable device comprising:
a signal interface configured to wirelessly communicate with a client device;

a memory storing information about a treatment regimen, a program related to a protocol to be followed by the portable device, and an identification code associated with said program;

a user interface configured to (i) display said stored information, (ii) receive data from a patient based on said stored information, and (iii) display said data received from said patient, said user interface comprising a multi-line presentation element, said multi-line presentation element capable of displaying multiple lines of text, wherein said stored information is displayed by said display as an alphanumeric message; and a processor configured to record a time said data is received from said patient in said memory and send said data received from said patient along with said identification code to said client device.

2. The portable device of claim 1, wherein said stored information, said program related to said protocol, and said identification code associated with said program are received from said client device.

3. The portable device of claim 1, wherein said user interface is further configured to notify said patient when to follow said treatment regimen.

4. The portable device of claim 1, wherein said user interface is further configured to receive data that patient has followed said treatment regimen.

5. The portable device of claim 4, wherein said display comprises a liquid crystal display (LCD).

6. The portable device of claim 1, wherein said signal interface comprises a docking station and said client device comprises a personal desktop computer.

7. The portable device of claim 1, wherein said signal interface comprises an infrared connection and said portable device further comprises a personal digital assistant.

8. The portable device of claim 1, wherein said signal interface comprises a radio-frequency connection and said portable device further comprises a cellular telephone.

9. The portable device of claim 1, wherein said signal interface comprises a plug-in connection and said client device comprises a hard-wired phone.

10. The portable device of claim 1, wherein said portable device comprises a hand-held computing device.

11. The portable device of claim 1, wherein said portable device comprises an application specific device.

12. The portable device of claim 1, wherein said portable device comprises a pager.

13. The portable device of claim 1, wherein said portable device comprises a personal notebook computer.

14. The portable device of claim 1, wherein said portable device comprises an Internet appliance.

15. The portable device of claim 1, wherein said client device comprises an Internet-enabled television.

16. The portable device according to claim 1, wherein said memory comprises a Flash memory.

17. A system comprising:

a portable device configured to receive a first information about a treatment regimen and send a second information about compliance with said treatment regimen, wherein said portable device comprises (a) a memory configured to store said first information regarding said treatment regimen, storing a program related to a protocol to be followed by the portable device, and configured to store identification data associated with the program and (b) a user interface capable of displaying multiple lines of text and receiving data from a patient, said user interface configured to display (i) said first information regarding said treatment regimen and (ii) said second information, wherein said first information is displayed as at least one alphanumeric message of at least a portion of one line of text and said second information comprises said data received from said patient based on said first information; and a client device configured to (i) receive said second information and said identification data associated with said program from said portable device and (ii) send said second information and said identification data associated with said program to a server, wherein said server compares said first information with said second information.

18. The system according to claim 17, wherein said client device receives said second information and said identification data associated with said program from said memory of said portable device.

19. A method comprising the steps of (A) receiving a first information about a treatment regimen by a portable device and inputting a second information about compliance with said treatment regimen into said portable device, (B) storing said first information regarding said treatment regimen, a program related to a protocol to be followed by said portable device, and an identification code associated with said program in a memory of the portable device, (C) receiving data from a patient with a user interface of the portable device capable of displaying multiple lines of text, (D) displaying said first information regarding said treatment regimen as one or more alphanumeric messages of at least one portion of a line of text with the user interface, (E) displaying said second information, wherein said second information comprises data received from a patient based on said first information; and (F) receiving said second information and said identification code associated with said program by a client device from said portable device and sending said second information and said identification code associated with said program to a server.

20. The method according to claim 19, wherein step (F) further comprises comparing said first information with said second information by said server.

* * * * *